United States Patent [19]

Ramage

[11] Patent Number: 5,892,007
[45] Date of Patent: Apr. 6, 1999

[54] METHOD AND MEANS FOR OLIGONUCLEOTIDE SEPARATION

[75] Inventor: Robert Ramage, Edinburgh, Great Britain

[73] Assignee: Laporte PLC, England

[21] Appl. No.: 532,712

[22] PCT Filed: Mar. 29, 1994

[86] PCT No.: PCT/GB94/00656

§ 371 Date: Feb. 1, 1996

§ 102(e) Date: Feb. 1, 1996

[87] PCT Pub. No.: WO94/22802

PCT Pub. Date: Oct. 13, 1994

[30] Foreign Application Priority Data

Apr. 2, 1993 [GB] United Kingdom .................. 9307014

[51] Int. Cl.$^6$ ........................... C07H 21/04; C07C 43/21; C07C 33/34
[52] U.S. Cl. .................... 536/23.1; 536/25.3; 536/25.31; 536/25.4; 536/25.41; 585/500
[58] Field of Search ............................... 536/25.3, 25.31, 536/25.4, 25.41, 23.1; 585/500

[56] References Cited

FOREIGN PATENT DOCUMENTS 2251242 7/1992 United Kingdom .
WO 92/09615 6/1992 WIPO .

OTHER PUBLICATIONS

R. Ramage et al., "–(17–Tetrabenzo[a,c,g,i] fluorenylmethyl)–4',4"–Dimethoxytrityl Chloride: A Hydrophobic 5'–Protecting Group for the Separation of Synthetic Oligonucleotides", vol. 34, 1993, pp. 7133–7136.

E. Happ et al., Nucleosides & Nucleotides, "New Trityl–based Protecting Groups with a Mild Two–Step Removal", vol. 7, 1988, pp. 813–816.

Primary Examiner—James O. Wilson
Attorney, Agent, or Firm—Klauber & Jackson

[57] ABSTRACT

A protecting group for use in separating oligodeoxyribonucleotide compounds having the formula Ar—L—Y, wherein Ar represents a substantially planar, fused ring system containing at least fused rings; L represents a linker group containing at least one carbon atom which is capable of bonding to Ar and Y; and Y represents a specifically acid labile group.

8 Claims, 4 Drawing Sheets

METHOD AND MEANS FOR OLIGONUCLEOTIDE SEPARATION

The present invention relates to a new protecting group and its use, in particular, in oligodeoxyribonucleotide synthesis. It relates more particularly to a protective group facilitating the purification of compounds, especially oligodeoxyribonucleotides (or oligonucleotides as more frequently known) during or at the end of a synthesis.

BACKGROUND OF THE INVENTION

Oligonucleotides are part of the sequence of a molecule of DNA. DNA is a polynucleotide; a polymer built of nucleotide units, each comprising a phosphate group, a sugar (deoxyribose), and a base (adenine, guanine, cytosine or thymine). DNA molecules form a double helix with the two strands held together by hydrogen bonds between specific base pairs: adenine always pairs with thymine and guanine with cytosine. Thus the sequence of one strand of the helix determines the sequence of the other:

5'... ATGAAATCTGTACATGGT ... 3'
5'... TACTTTAGACATGTACCA ... 5'

The sequence of a particular piece of DNA might represent part of a gene which 'encodes', and thus directs the production of, a particular protein. Protein production is mediated via an RNA copy of this DNA (with uracil in place of thymine), where the order of these bases defines the order in which the amino acids are joined together to form proteins. Because there are 20 amino acids but only four bases, it follows that a group of bases is needed to code for one amino acid. These groups are comprised of three bases called 'codons'. Thus methionine is coded for by ATG, histidine by CAT, lysine by AAA, proline by CCT etc, and the DNA sequence 5'ATGAAACCTCATAAA 3' codes for the amino-acid sequence Met-Lys-Pro-His-Lys. Altering the DNA sequence by substituting one base for another can alter the encoded amino acid sequence. For example, if the CCT codon in the DNA sequence 5'ATGAAACCTCATAAA 3' is changed to CAT (a single nucleotide C to A substitution) the resulting amino acid sequence changes from Met-Lys-Pro-His-Lys to Met-Lys-His-His-Lys. This ability to change, or 'mutate', the nucleotide sequence of a gene or DNA fragment is the basis behind the technique known as site-directed mutagenesis. A known DNA sequence is usually mutated with the aid of a synthetic oligonucleotide and is therefore often called oligonucleotide-directed mutagenesis.

The critical feature of site-directed mutagenesis is that it allows pre-designed mutations to be specifically introduced into a target gene. With the structures of many important proteins having been determined at atomic resolution, particularly by X-ray crystallography but also by NMR spectroscopy, it is possible to analyze the structure and function of enzymes in great detail. The importance of one or more amino acid residue can be assessed by engineering specific modifications into the protein structure. Most commonly the mutations involve single base substitutions but it is also possible to construct deletions and insertions in the DNA sequence, resulting in shorter or longer polypeptides.

It can therefore be seen that there is a need to be able to synthesise oligonucleotide sequences of a high purity. Further information regarding site directed mutagenesis is to be found in an article by Chapman and Reid in Chemistry in Britain, March 1993, p 202–204.

In organic synthesis, in particular multi-step, organic synthesis, the purification of the products obtained can present more problems than the synthesis itself. This is particularly true in the case of oligonucleotide synthesis, a synthesis which systematically uses protective groups which can also play supplementary roles. One solution to this problem would be to modify the oligonucleotide, or any other molecule requiring protection, by binding it to a solid in a manner which is physically reversible, in the course of working up and purification. To date no protective group has been disclosed as being capable of exercising such a property.

GB-A-2251242 (Ramage et al) describes a protecting group for use in peptide synthesis. The protecting group is of formula Ar—L— where Ar represents a substantially plane, fused ring system containing at least 4 aromatic rings and L represents a group containing at least one carbon atom which is capable of bonding to a group to be protected, which may be an N-terminal amino group of an α-amino acid in the synthesis of peptides. The protecting groups improve the purification of crude peptides by affinity chromatography on porous graphitised carbon (PGC) HPLC columns.

The protecting groups disclosed in GB-A-2251242 are based on tetrabenzo (a,c,g,i) fluorene (Tbf). However this is a base labile group. In oligonucleotide synthesis several basic treatments are carried out, e.g. phosphate deprotection, and therefore this base labile protecting group is unstable in oligonucleotide synthesis. It is also important that the protecting group for oligonucleotide synthesis can be removed under mild acidic conditions. The protecting group should also only require simple reaction conditions for its introduction onto a nucleotide. The molecule should be regioselective as it is important that the 3'-hydroxyl of the nucleotides remains unprotected. It is also preferable that the molecule should enable monitoring of reactions and purifications.

SUMMARY OF THE INVENTION

The present invention provides a protecting group of formula (I):

Ar—L—Y—            (I)

where Ar represents a substantially plane, fused ring system containing at least 4 aromatic rings;

L represents a linker group containing at least one carbon atom which is capable of bonding to Ar and Y; and Y represents a specifically acid labile group.

The groups Ar and Y are separated by a linker group, L, preferably a saturated alkyl group.

The group Ar is as defined in GB-A-2251242, with the same subgroup being preferred.

The acid labile group Y may be selected from groups known in the art, e.g. pixyl and trityl groups and derivatives thereof. Trityl and derivatives thereof, e.g. methoxy substituted trityl, are particularly preferred.

The molecules protected by the group defined above have been found to adsorb very strongly to reverse phase silica gel or polystyrene. This adsorption is reversible. The more aromatic rings carried by the group, the better is the adsorption and the longer the time required for elution, and vice versa. The optimum can be defined case for particular cases by those skilled in the art. However, a number of 4 to 8 aromatic rings in addition to the central ring in general constitutes a satisfactory compromise both from the economic point of view and from the point of view of the adsorption and elution criteria.

The present invention also provides a protecting compound comprising a group as defined above attached, via the Y group, to a leaving group, such as a group which contains a nitrogen, oxygen, sulphur, selenium, tellurium, silicon or halogen atom. Examples of leaving groups are halogen atoms (e.g. F, Cl, Br or I) or —OH, —NH$_2$, —SO$_3$C$_6$H$_4$—pCH$_3$, —SH, or —CN groups.

The groups according to the invention have another particularly advantageous characteristic, that is to say the great majority of them are adsorbers of visible or ultraviolet radiation in wavelengths which differ from those for natural nucleosides.

This property enables devices to be developed comprising, for successive or simultaneous use:
a) a chamber, for example a column, filled with a suitable substrate, such as reverse phase silica gel or polystyrene, and
b) a kit for grafting a protective group as defined above on a molecule.

The kit for grafting the protective group comprises the various reagents known to those skilled in the art for grafting a protective group on a molecule to be protected.

This device is advantageously completed by (c) a fraction-collecting system fitted with an ultraviolet (UV), visible spectroscopic, or fluorescent spectroscopic detector.

Thus, it has been possible to develop a new process for synthesis and/or separation of molecules, in particular oligonucleotides, which comprises the following steps:
protecting at least one group in at least one compound in a mixture of compounds to be separated with a group as defined above, and
passing the mixture of compounds through a chamber filled with a reverse phase silica or polystyrene material.

The present invention also provides use of a group as defined above to protect at least one functional group of a molecule.

The present invention is now further described and illustrated.

Synthesis of Oligonucleotides

Figure 1:
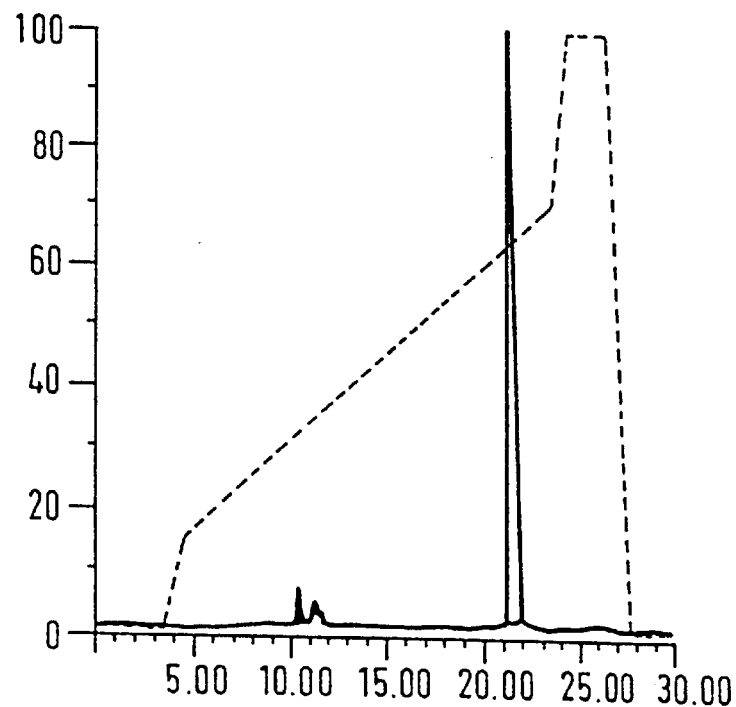
FIG. 1 shows the spectrum of sequence 10, i.e. 5'-DMTr-TCG-AGT-3', obtained by a RP-HPLC run.

An oligonucleotide chain may be illustrated as:

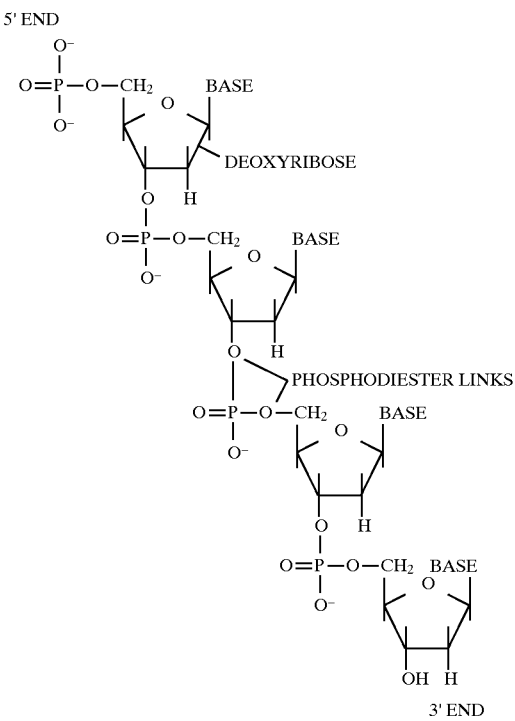

The bases may be selected, as described above, from adenosine, thymine, guanine, cytosine and uracil may also be used.

In synthesising oligonucleotides, the first deoxyribonucleoside can be considered as being linked to a polymer, i.e.

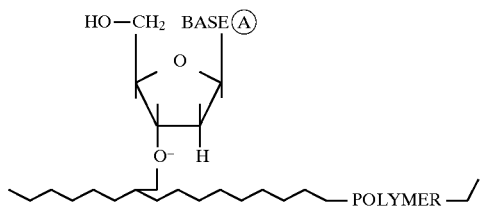

However, because links are carried out via the 3' site of the deoxyribonucleoside, it is necessary to protect the 5' hydroxyl group of the deoxyribonucleoside to ensure it does not react. This protecting group must be cleavable in order that progressive linkage can continue. Work has shown that the trityl group, or 4'-methoxy derivatives, is a particularly suitable protecting group. It can be removed by mild acidolysis. Thus, the first deoxyribonucleoside linked to the polymer can more accurately be represented as

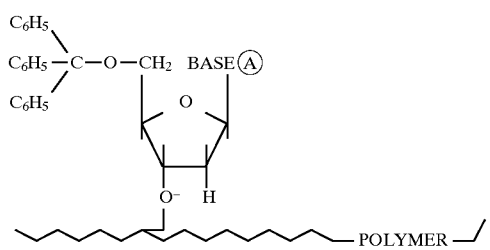

wherein the 3' hydroxyl group of the 5' protected nucleoside has reacted with the polymer support.

Khorana et al describe linkage of the trityl group in a number of articles, e.g. J.Amer. Chem. Soc., 1962, 84, 430–440.

In order to form the next part of the chain, a 3' 5' phosphodiester bond must be formed. Therefore the protected 5' group is deprotected by mild acidolysis. The molecule

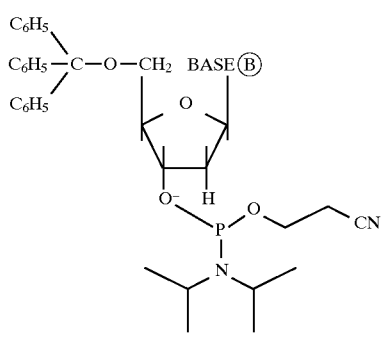

is added. The highly reactive 3' phosphorous group of this new molecule reacts with the deprotected 5' hydroxyl of the first attached molecule to form, after oxidation, a two member chain linked by a phosphodiester group. This is a standard procedure well known in the art.

The procedure is repeated to form the desired oligonucleotide. However, the reaction to join the nucleotides does not proceed at 100% yield. Incorrect —OH terminated chains are therefore formed. These may be capped by methods known in the art, e.g. by the use of acetic anhydride. The capping reaction is carried out at the end of each cycle of the process.

At the final step, the protecting group of the invention is added, preferably attached to the terminal deoxyribonucleotide. This will only add to the desired oligonucleotide chains, as the incorrect chains have been capped.

This final cycle therefore yields

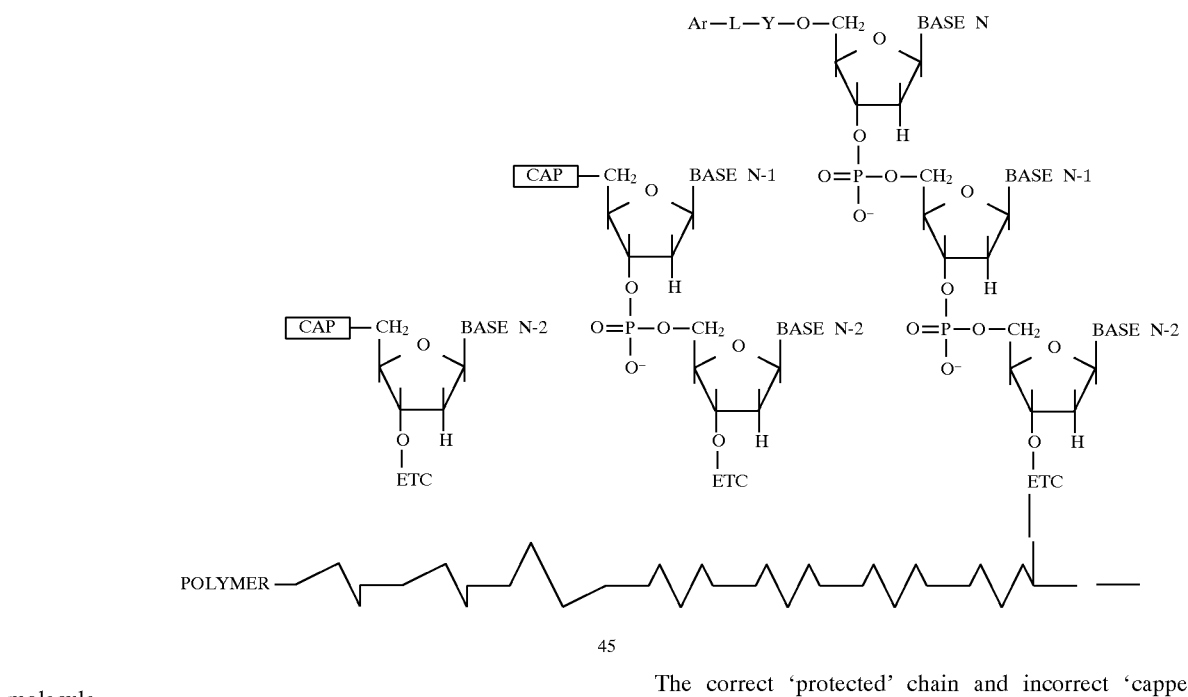

The correct 'protected' chain and incorrect 'capped' chains are then cleaved from the polymer substrate. The correct and incorrect chains are passed into contact with the silica or polystyrene substrate.

The hydrophobic properties of the protecting groups Ar—L—Y enables the product to be retained on the substrate. The capped, non-hydrophobic unprotected chains are not retained and therefore wash through during elution.

Finally, mild acidolysis removes the desired oligonucleotide chain from the protecting group as the acid labile group is cleaved.

The link between the Ar group and the substrate may be broken to regenerate the substrate for further use.

It will be seen that there may be provided either the novel protecting group per se, or the novel protecting group linked to any of 4 bases for use as the final part of the oligonucleotide.

EXAMPLES

In order to clarify the following Examples, it will be of assistance to note the numbering conventionally used in the tetrabenzofluorene molecule:

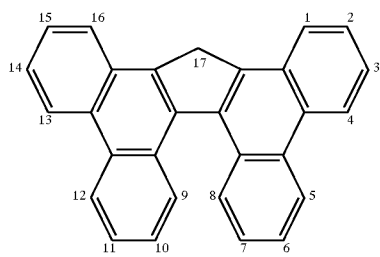

1. Diphenyl,-(4-(tetrabenzofluoren-17-yl-methyl)-phenylcarbinol and analogues.

n-Butyl-lithium was added to tetrabenzofluorene in dry THF at −78° C. under argon and subsequently methyl-(4-bromomethyl)-benzoate was added. After usual work-up a pale yellow solid is obtained in 60% yield. Compound 16 is fluorescent. A Grignard reaction with compound 16 and bromobenzene yielded the corresponding tritanol 17. The latter compound was obtained in 63% yield and was very crystalline and fluorescent. Starting from 9-bromophenanthrene compound 17 could be obtained in an overall yield of 26%. Before compound 17 could be used to protect a nucleoside the trityl chloride derivative 18 was generated with an excess of acetyl chloride in benzene at reflux. Compound 18 was not isolated but was immediately dissolved in dry pyridine and added to a solution of thymidine, triethylamine and traces of DMAP in dry pyridine. After reaction overnight and usual work-up a white solid, compound 19 was obtained in 35% yield. In the latter reaction excess of the unreacted starting material 17 could be regenerated from chromatographic fractions.

In order to increase the acid lability of 19 compounds 20 and 21 and 22 were synthesised bearing two electron donating methoxy groups, similar yields were obtained in this case.

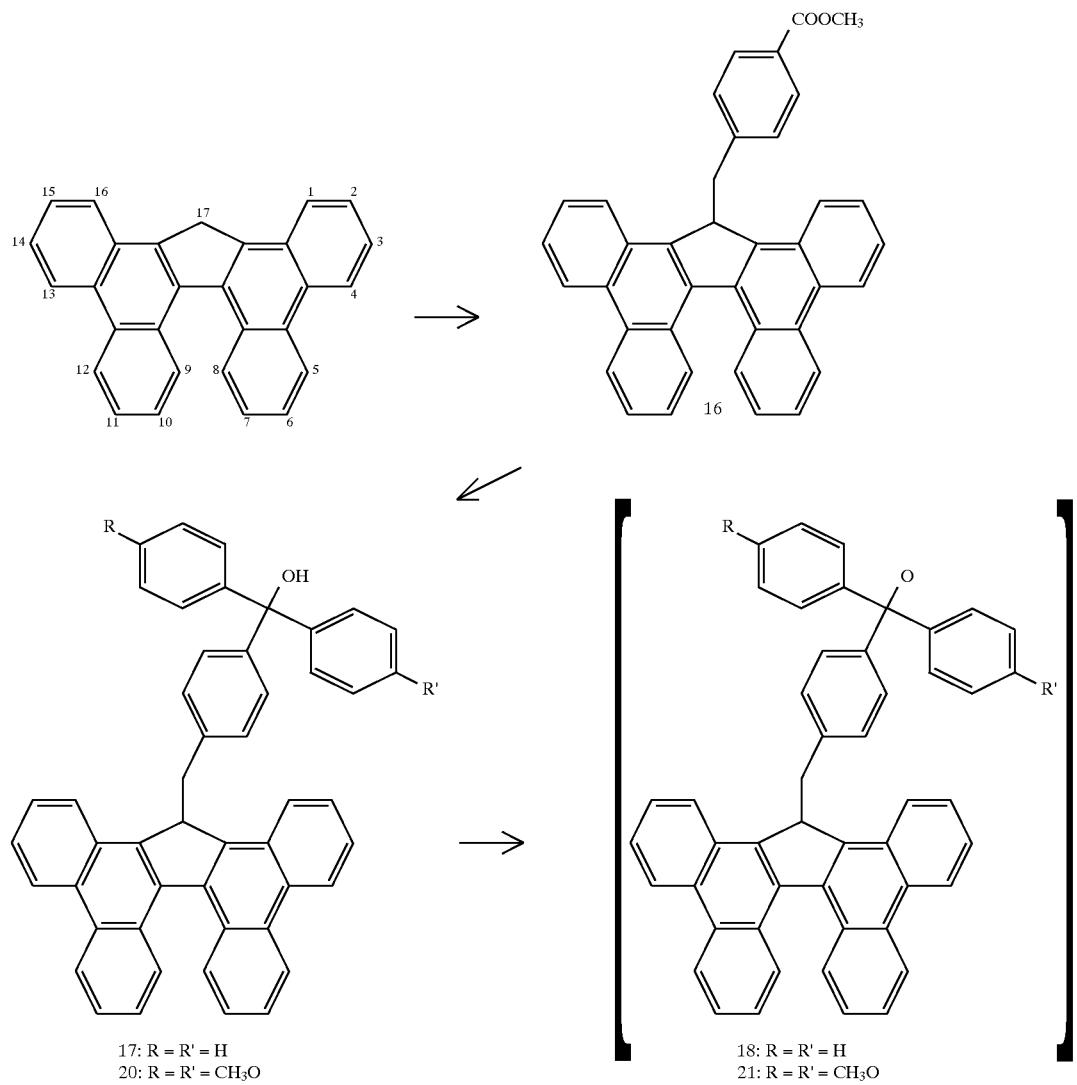

-continued

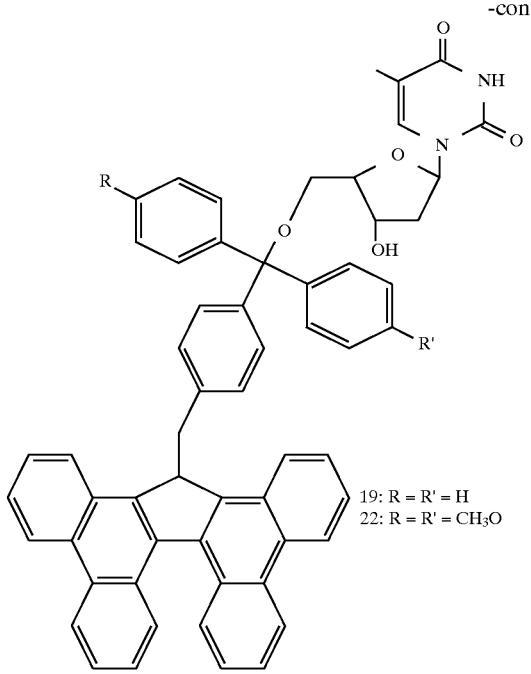

19: R = R' = H
22: R = R' = CH₃O

2. Kinetic study of the deprotection

The deprotection rates of the newly protected thymidine compounds 19 and 20 were compared with the deprotection rate of the commonly used 5'-DMTr-thymidine Dimethoxytrityl-thymidine nucleoside. The deprotection is carried out in acidic conditions. It generates a colourful (deep orange) carbocation whose adsorbance maximum is at 500 nm. Therefore the deprotection reaction of thymidine in a UV experiment could be studied, measuring the adsorbance at 500 nm against time. In order to perform the deprotection in a realistic time scale, 80% acetic acid/acetonitrile solutions were used and a temperature of 50° C. The deprotection was considered as a first order rate reaction and plotting $Ln((1-A_t)/A)$ against time gave the reaction rate from the gradient.

Rate constant of 5'-DMTr-T=0.0018 s$^{-1}$

Compound 22=0.0037 s$^{-1}$

Compound 19=not detected

Compared to DMTr-thymidine the deprotection of thymidine was found to be twice as fast when using our new protecting group 20 under the same conditions. On the other hand the rate of deprotection of compound 19 could not be determined under the same conditions as it is much slower than the rate of 22 and 5'-DMTr-T.

3. Affinity to carbon graphite

In an experiment designed to show the affinity of the Tbf group to carbon graphite, both compound 22 and 5'-DMTr-thymidine were dissolved in methanol and some carbon graphite later added. The HPLC trace of the mixture before carbon was added, shows clearly the difference in hydrophobicity of the two compounds on a RP-18 column. The retention time of 22 is almost twice as long than 5'-DMTr-thymidine, sample of the solution was injected after treatment with graphite and no compound 22 peak could be observed. This result demonstrates clearly that thymidine protected with 20 bearing the Tbf, structure is totally retained on carbon graphite.

5'O-Tbf-DMTr-Nucleoside-Phosphoramidites

Compound 1 was reacted with N,N-diisopropyl β-cyanoethyl phosphoramidyl chloride 2 in anhydrous, oxygen free conditions, to give the desired phosphoramidite 3 in high yields.

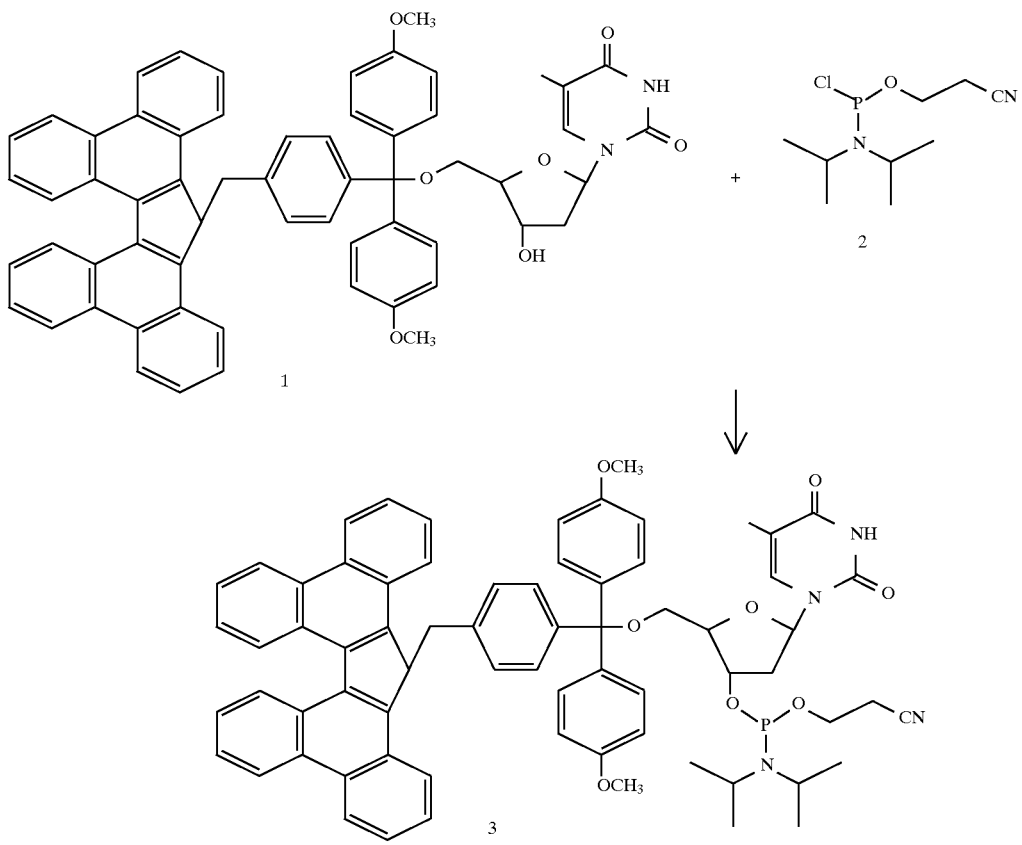

Figure 2:
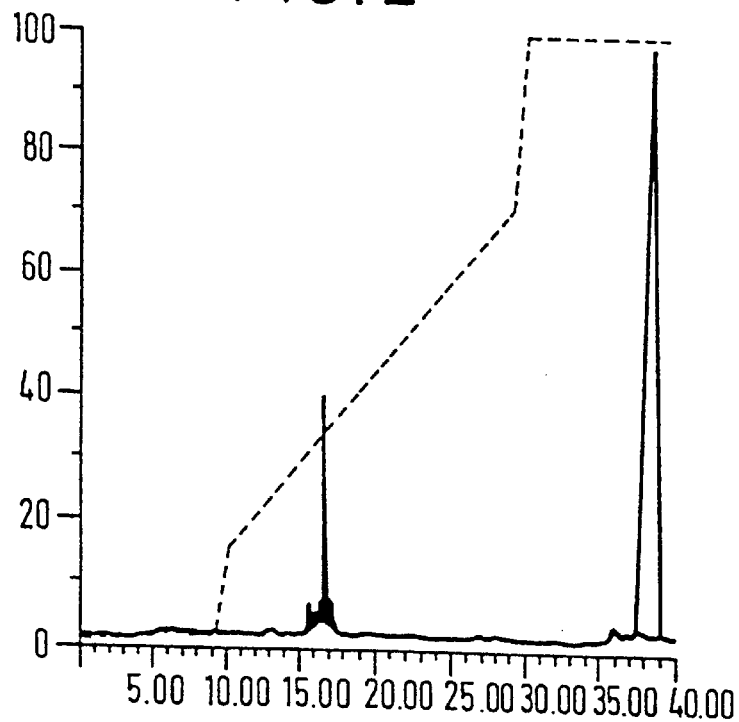
FIG. 2 shows the spectrum of sequence 11, i.e. 5'-Tbf-DMTr-TCG-AGT-3', obtained by a RP-HPLC run.

Advantageously 3 could be isolated by precipitation in cold n-hexane, thus avoiding a chromatographic purification. Subsequently a series of oligonucleotides 4 were synthesised on an ABI DNA Synthesizer using the standard protocol for the phosphoramidite chemistry, 1 μmol scale, coupling time 30 s. A 0.1M solution of 5'-O-thymidine phosphoramidite in acetonitrile/dichloromethane 9/1 was connected to a port on the machine. Several oligonucleotides were made starting with a polythymidine 12-mer and later randomly selected 6-mer and 12-mer base sequences. All these sequences had a 5'-T end. A coupling time of 5 Min instead of 30 s was chosen for the last coupling steps. In each case, a crude oligonucleotide solution in ammonium hydroxide was obtained that was strongly fluorescent under UV light, 254 nm. Control sequences that were left with the normal DMTr group at the 5'-end did not fluoresce, as expected. This qualitative observation was a clear indication that the modified thymidine monomer had coupled to the oligonucleotide chain.

protecting group in pyridine was used although in the case of Tbf-DMTr-Cl a precipitate was formed after 30 min, probably due to a cool ambient temperature. After heating, the precipitate dissolved again, a lower concentration could be used to eliminate this problem. FIGS. 1 and 2 show the RP-HPLC runs of sequences 10 and 11 respectively. Both sequences were obtained in 90% yield. In this experiment it could be proved that Tbf-DMTr can be tagged on to a support bound 6-mer oligonucleotide with similar efficiency to DMTr.

Purification of oligonucleotides

The importance of a good separation technique for synthetic oligonucleotides is often neglected. Since the impurities from a large number of reactions are stored up on the support, these must all be resolved, preferably in a single chromatographic step. HPLC is suitable for purification of perhaps up to 50 mg of oligonucleotide but requires an expensive hardware. The original design of Tbf-DMTr was intended to be used in an affinity based separation, notably

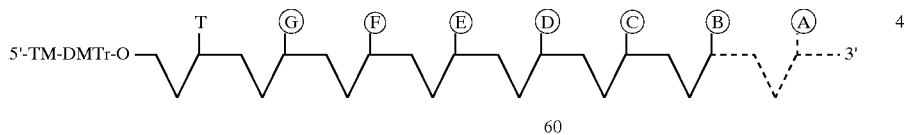

Two oligonucleotides 10 and 11 were synthesized.
(10): 5'-DMTr-TCG-AGT-3'
(11): 5'-Tbf-DMTr-TCG-AGT-3'

Both oligonucleotides were synthesized with the trityl-off mode and were subsequently reacted on solid phase with their respective 5'-OH protective group by the "push-pull" method. The reaction times were 2 h. A 0.5M solution of the to PGC. The highly lipophilic property of Tbf-DMTr was applied to an alternative separation procedure of oligonucleotides from their impurities.

Purification on C18 silica gel cartridges

Figure 4:
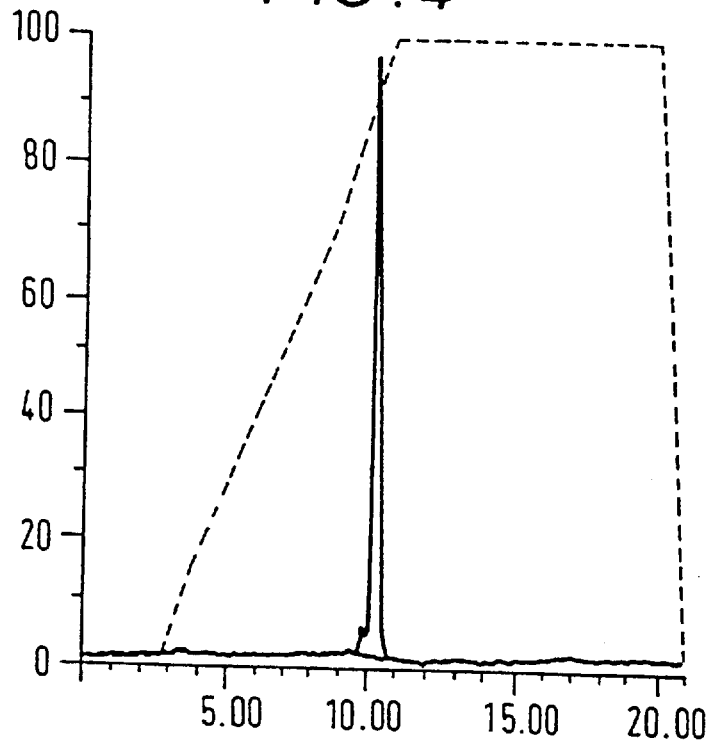
FIG. 4 shows the spectrum obtained by a HPLC run of deletion oligos without any of the Tbf-DMTr-bound oligonucleotide.
Figure 5:
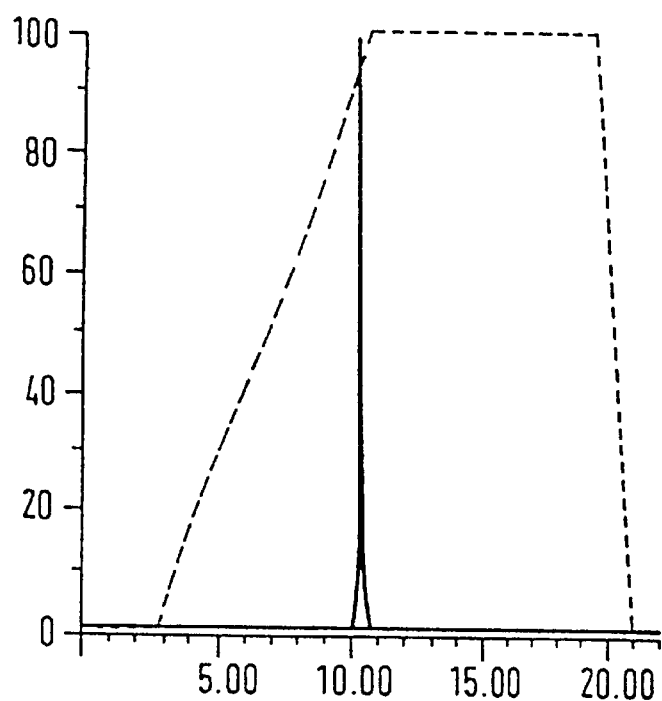
FIG. 5 shows the spectrum obtained by a HPLC run of the pure oligonucleotide after deprotection on a C18 silica gel cartridge.

Reverse phase silica chromatography separates a mixture of compounds according to their hydrophobicity. A simple purification method, based on the fact that Tbf-DMTr attached oligonucleotides are much more hydrophobic than normal oligonucleotides, was developed. This new method makes use of 1.5 cm long polypropylene cartridges, packed with C18 silica gel, commercialised by Waters under the brand name SEP-PAK. These small columns are normally used for desalting peptides. They contain an inlet and an outlet which can be connected to a syringe. These cartridges are easily available and are cheap. In a first experiment we determined at which solvent mixture the failure sequences and the Tbf-DMTr-bound oligonucleotide would elute on C18 silica gel. With analytical HPLC, using the same conditions as described above, we carried out a series of isocratic runs with the crude solution of 5. The results showed that the failure sequences started to elute with 10% of solvent B but that all of them eluted with 20% of B. The Tbf-DMTr-oligo did not elute until 80% of B. This experiment indicated which solvent mixture to use for the purification of SEP-PAK cartridges. Next, we loaded about 20 OD units of the crude oligonucleotide 5 onto a cartridge and monitored the eluate by analytical HPLC. The best loading was obtained with a flow rate of about 1 drop every 2 s. Under UV light, 254 nm, a clear narrow fluorescent band could be observed at the top of the cartridge. The deletion oligos were eluted with 10% acetonitrile/90% 0.1M NH$_4$OAc without any of the Tbf-DMTr-oligo, as can be seen on the HPLC spectrum FIG. 4, retention time=10.5 min. On Spectrum FIG. 5 we can see the pure oligonucleotide after deprotection on the cartridge and elution with 20% acetonitrile/80% 0.1M NH$_4$OAc, retention time=10.5 min.

Figure 3:
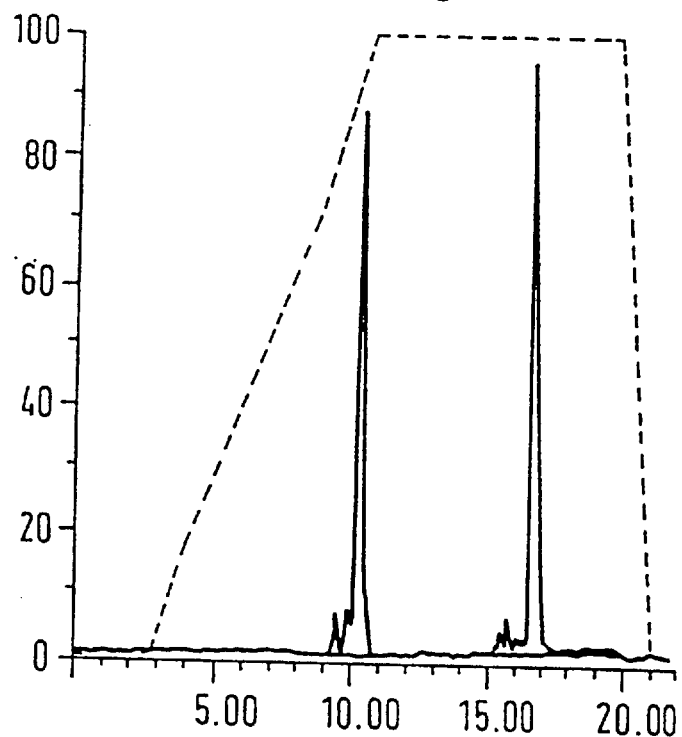
FIG. 3 shows the spectrum obtained by a HPLC run of a crude solution of a Tbf-DMTr-bound oligonucleotide.

Looking at the quality of crude 5 on FIG. 3 we managed to purify this oligonucleotide with a simple procedure. These experiments were repeated with various batches of 12-mers and a 6-mer with loading of a 1 μmol scale synthesis. It is therefore possible to draft a simple 7 points procedure for the SEP-PAK purification of short oligonucleotides:

1. Flush the cartridge with 5 ml acetonitrile, followed by 5 ml 0.1M NH$_4$OAc with a properly adapted syringe.
2. Take the crude ammonia solution, evaporate it, and dissolve the crude oligonucleotide in 2 ml of 0.1M NH$_4$OAc. Place the solution in the syringe and slowly push it through the cartridge.
3. Slowly wash the cartridge with 2×5 ml of 10% acetonitrile/90% 0.1M NH$_4$OAc.
4. Wash the cartridge with 5 ml of deionized water.
5. To deprotect the Tbf-DMTr bound oligonucleotide, push ca. 2 ml of a 2% solution of trifluoroacetic acid in water and wait 10 min.
6. Flush the cartridge with 5 ml of deionized water.
7. Elute the purified oligonucleotide by washing the cartridge with 2 ml of 20% acetonitrile/80% 0.1M NH$_4$OAc.

The purification method described above has been carried with DMTr bound oligonucleotide and seems to give inconsistent results. The fact that Tbf-DMTr is much more lipophilic than DMTr allows us to be more flexible in the solvent mixture choices. The purification of an oligonucleotide could be reduced to 15 min instead of 2 h on preparative HPLC. Next we will study the purification of longer oligonucleotide by the same method.

Purification on polystyrene cartridge

Figure 6:
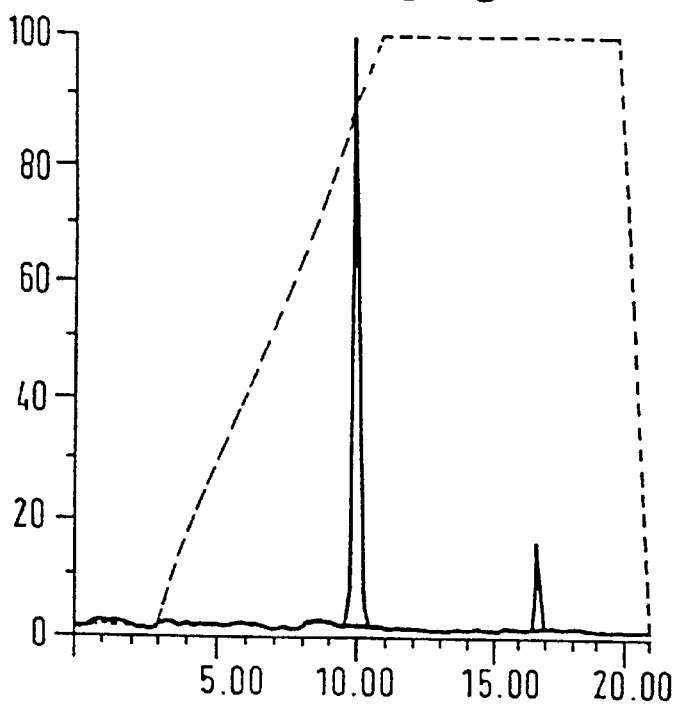
FIG. 6 shows the spectrum obtained by a HPLC run of the eluate failure sequences when the Tbf-DMTr-bound oligonucleotide was eluted on a polystyrene cartridge.
Figure 7:
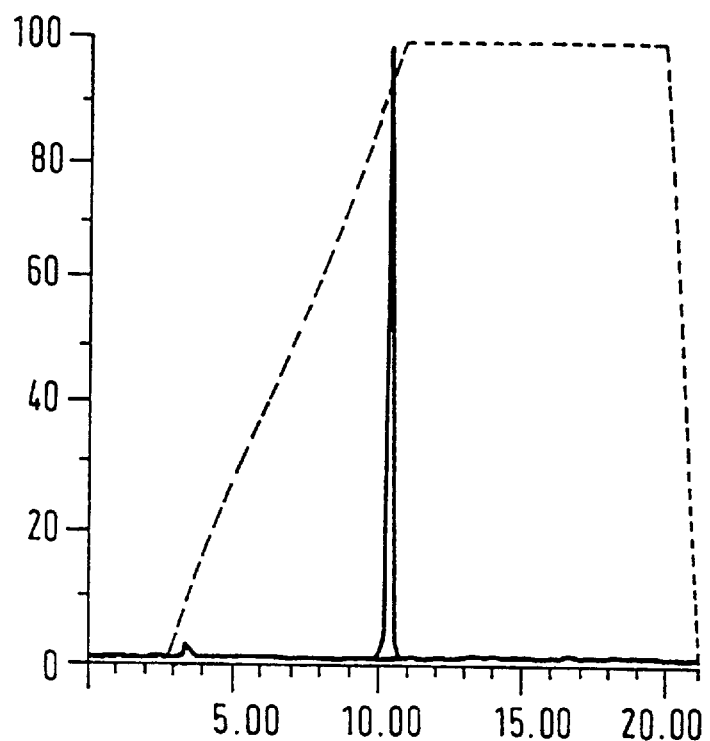
FIG. 7 shows the spectrum obtained by a HPLC run of the eluate consisting of pure oligonucleotide after deprotection and elution on a polystyrene cartridge.

We purchased similar cartridges from ABI but packed with polystyrene beads. Polystyrene columns have the advantage over C18 silica gel columns to be stable at all pH. We carried out the purification of an oligonucleotide of the sequence (A) with the same protocol as used for SEP-PAK cartridges. Spectrum FIG. 6 shows the eluate of failure sequences. A small amount of Tbf-DMTr bound oligonucleotide broke through the column but could be reloaded by passing the eluate through the column once again. This breakthrough is probably due to the poor packing of the cartridges, which leaves an empty space. After deprotection the pure oligonucleotide was eluted, spectrum FIG. 7. Therefore, we were able to show that this newly developed purification method, is applicable with a polystyrene stationary phase. Because of the stability of polystyrene cartridges in ammonia (pH>10) the crude solution of oligonucleotide can be directly loaded without prior evaporation.

Conclusion

The design of Tbf-DMTr-Cl has proven to be very useful in the purification of oligonucleotides. A simple procedure for the solid-phase reaction of Tbf-DMTr-Cl with the 5'-terminus of oligonucleotides has been developed. The purification protocol of oligonucleotides has become simpler, making use of small RP-C18 or polystyrene cartridges. The somewhat difficult purification of small genes can now be envisaged.

I claim:

1. An oligodeoxyribonucleotide protecting group of the formula (I):

where Ar represents a substantially plane, fused ring system containing at least 4 aromatic rings;

L represents a saturated alkyl group capable of bonding to Ar and Y;

and

Y represents a acid labile group selected from pixyl or trityl groups or derivatives thereof.

2. A protected oligodeoxyribonucleotide compound comprising a protecting group as claimed in claim 1 wherein the protecting group is attached to an oligodeoxyribonucleotide, via the Y group, to a leaving group present on said oligodeoxyribonucleotide.

3. A protected oligodeoxyribonucleotide compound as claimed in claim 2 wherein the leaving group is selected from the group consisting of a halogen atom, —OH, —NH$_2$, —SO$_3$, C$_6$H$_6$—pCH$^3$, —SH and —CN groups.

4. A protected oligodeoxyribonucleotide compound comprising a protecting group as claimed in claim 1, and an oligodeoxyribonucleotide.

5. A protecting group as claimed in claim 1, wherein Ar contains at least 6 aromatic rings.

6. A protecting group as claimed in claim 1, wherein the aromatic rings are hexagonal.

7. A protecting group as claimed in claim 1, wherein Y represents a methoxy substituted trityl group.

8. A process for the separation of oligodeoxyribonucleotide compounds which comprises (a) protecting at least one group in at least one compound in a mixture of compounds to be separated with a protecting group as claimed in claim 1 and (b) passing the mixture of compounds through a chamber filled with a reverse phase silica gel or polystyrene material, thereby retaining on said silica gel or polystyrene material at least one compound containing said protecting group and not retaining on said silica gel or polystyrene material those compounds not containing said protecting group.

* * * * *